United States Patent [19]

Ismach

[11] Patent Number: 4,813,409
[45] Date of Patent: Mar. 21, 1989

[54] VENTILATOR SYSTEM HAVING IMPROVED MEANS FOR ASSISTING AND CONTROLLING A PATIENT'S BREATHING

[76] Inventor: Aaron Ismach, 335 Castle Dr., Englewood Cliffs, N.J. 07632

[21] Appl. No.: 780,977

[22] Filed: Sep. 27, 1985

[51] Int. Cl.[4] ............................................. A61M 16/00
[52] U.S. Cl. ............................ 128/204.28; 128/205.24
[58] Field of Search .................... 128/203.25, 204.24, 128/204.26, 204.28, 204.23, 205.16, 205.23, 202.22

[56] References Cited

U.S. PATENT DOCUMENTS

| | | | |
|---|---|---|---|
| 3,251,359 | 5/1966 | Ismach | 128/205.16 |
| 3,556,095 | 1/1971 | Ismach | 128/201.28 |
| 3,730,180 | 5/1973 | Davison | 128/204.24 |
| 3,890,967 | 6/1975 | Elam et al. | 128/205.23 |
| 3,896,837 | 7/1975 | Rohling | 128/203.28 |
| 3,898,987 | 8/1975 | Elam | 128/205.23 |
| 3,903,881 | 9/1975 | Weigl | 128/204.26 |
| 3,905,362 | 9/1975 | Eyrick et al. | 128/202.22 |
| 3,910,270 | 10/1975 | Stewart | 128/201.24 |
| 4,051,847 | 10/1977 | Henken | 128/202.22 |
| 4,082,043 | 4/1978 | Fry et al. | 128/204.26 |
| 4,141,354 | 2/1979 | Ismach | 128/204.28 |
| 4,141,356 | 2/1979 | Smargassi | 128/204.23 |
| 4,237,928 | 12/1980 | Urushida | 128/203.25 |
| 4,266,573 | 5/1981 | Braatz | 128/203.25 |

Primary Examiner—Edward M. Coven
Assistant Examiner—K. M. Reichle
Attorney, Agent, or Firm—Edward H. Loveman

[57] ABSTRACT

A ventilator system which incorporates a pneumatic circuit having a breathing assistor and positive end expiratory pressure module assembly for assisting, controlling and monitoring a patient's breathing. Settings of the operating points of a breathing assistor sensor and a positive end expiratory pressure sensor are coordinated in the module assembly and track at a selected pressure differential. The system also includes a circuit for instantly dumping breathing gas without retard or throttling when gas pressure rises to a predetermined maximum value.

11 Claims, 3 Drawing Sheets

VENTILATOR SYSTEM HAVING IMPROVED MEANS FOR ASSISTING AND CONTROLLING A PATIENT'S BREATHING

In the following disclosure, the term PEEP appears frequently. This is an acronym for "positive end expiratory (or exhalation) pressure". Also the term "patient circuit" is used as an abbreviation of the term "Patient Breathing Circuit".

BACKGROUND OF THE INVENTION

1. Field of the Invention

This invention relates to a ventilator system for controlling, assisting and monitoring a patient's breathing and more particularly concerns improvements in the ventilator system described in my prior U.S. Pat. No. 4,141,354. The improvements are especially concerned with a novel pneumatic PEEP/ASSIST circuit and with an improved pneumatic circuit for limiting the breathing gas pressure directed to a patient using the system.

2. Description of the Prior Art

In my prior U.S. Pat. No. 4,141,354, two separate pneumatic circuits were provided to permit the operator of the ventilator system to use the system as a breathing controller, with or without PEEP, or as an assistor-controller. When the prior system was used as a breathing assistor-controller, there was no convenient provision for also employing PEEP in an assist compensated mode. For example, if the ASSIST setting was established at a given value, say $-2$ cmH$_2$O, and at PEEP settings of 10 and 15 cmH$_2$O, the inspiratory efforts which would be the sum of the PEEP setting and the ASSIST setting cannot be obtained by the patient.

The ventilatory system described in my abovementioned prior patent, employed a spring loaded safety valve to dump breathing gas when pressure in the patient breathing circuit exceeded a preset magnitude determined by the spring bias in the valve. This type of valve is always characterized by throttling during its operation. When the pressure in the patient breathing circuit exceeds the preset magnitude of the spring bias, the valve theoretically opens to dump gas to prevent a pressure rise above the preset magnitude. In practice, due to the throttling characteristic of the valve, a retard occurs in the dumping action, so that the pressure in the patient's breathing circuit can greatly exceed the preset magnitude or value desired, particularly at high inspiratory flow rates, when the dumping action cannot keep up with the introduction of breathing gas into the breathing circuit.

SUMMARY OF THE INVENTION

It has been found highly desirable to employ PEEP while using the system as a breathing assistor-controller, and to have the setting of PEEP and ASSIST compensated or coordinated so that they track at a fixed differential. The operator can dial in any desired value of PEEP and will know that a predetermined inspiratory effort by the patient will initiate an inspiration. For example, if the operator sets the PEEP at 10 cmH$_2$O pressure, a predetermined inspiratory effort by the patient, $-2$ cmH$_2$O for example, (when pressure in the patient's breathing gas supply line falls to 8 cmH$_2$O) will initiate an inspiration. Similarly at a PEEP setting of 15 cmH$_2$O, a patient's inspiratory effort of $-2$ cmH$_2$O (patient's airway pressure drops to 13 cmH$_2$O) will initiate an inspiration.

The invention combines the two prior PEEP and ASSIST circuits into one novel circuit having a combination of pneumatic components and elements to achieve the abovementioned desirable results. At the same time the invention insures stability of ASSIST settings and prevention of pressure transients in the patient's breathing circuit from inadvertently causing premature actuation of inhalation assist during the patient's exhalation stage.

With respect to pressure limiting, the present system has no throttling or retard action to dumping of breathing gas. This insures maximum attainment of the preset pressure setting, independent of the inspiratory flow rate. This is accomplished by a novel arrangement of pneumatic components and circuit which employs the exhalation valve assembly in the patient breathing circuit, as the dumping means, to attain true pressure limiting.

These and other objects and many of the attendant advantages of this invention will be readily appreciated as the same becomes better understood by reference to the following detailed description when considered in connection with the accompanying drawings which:

DESCRIPTION OF THE PREFERRED EMBODIMENTS

Figure 1:
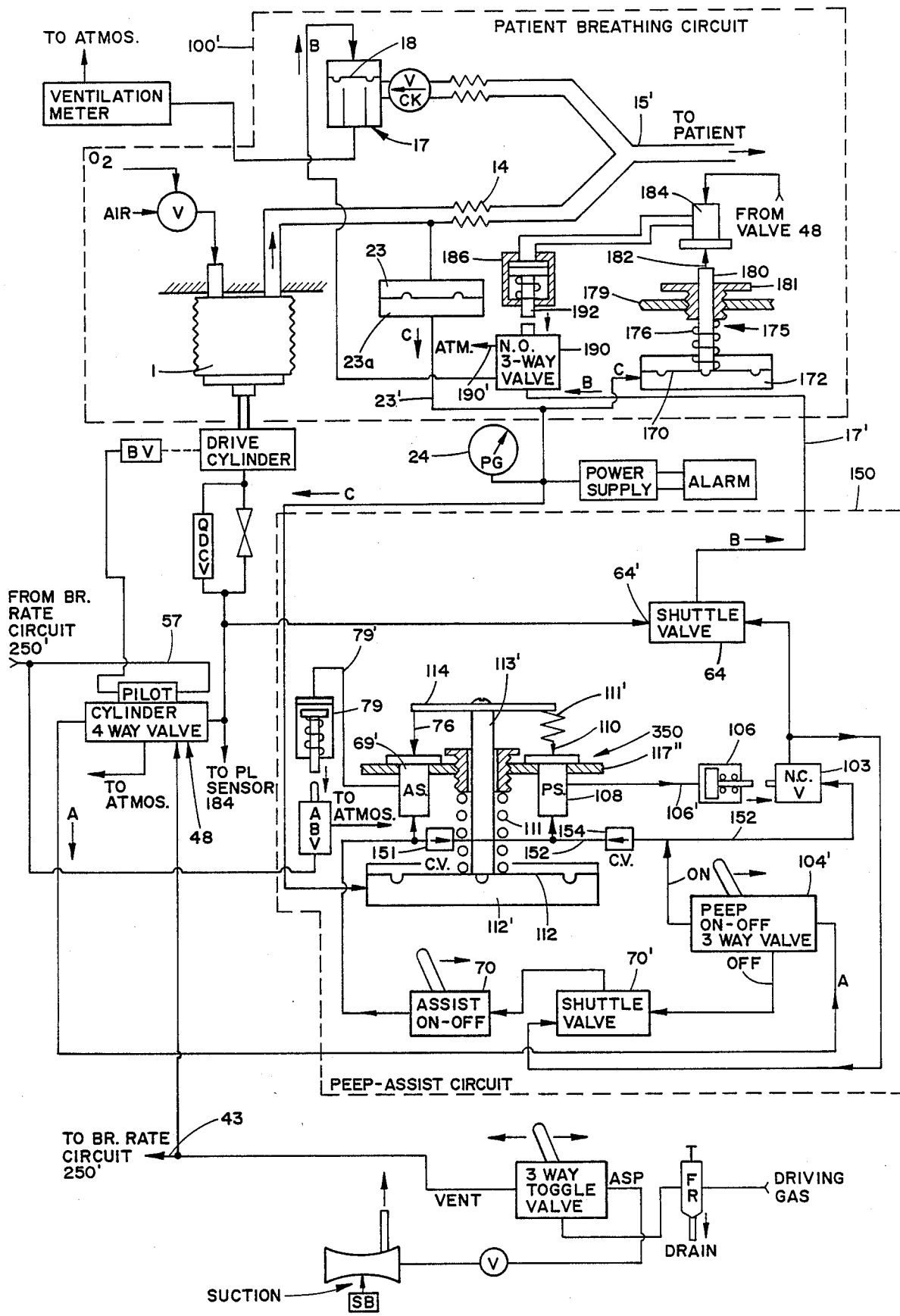
FIG. 1 is a schematic diagram of a ventilator system embodying the invention.

In the drawings, it will be noted that a number of components are not numbered. It will also be noted that these unnumbered components are not referred to in the following description. Reference should be made to my prior U.S. Pat. No. 4,141,354 for an explanation of those unnumbered components that are not referred to specifically herein because they are not parts of the system improvements which are the subject of the present invention and disclosure. The unnumbered components function in the ventilator system in the manner already described in detail in the abovementioned U.S. Pat. No. 4,141,354.

Figure 3:
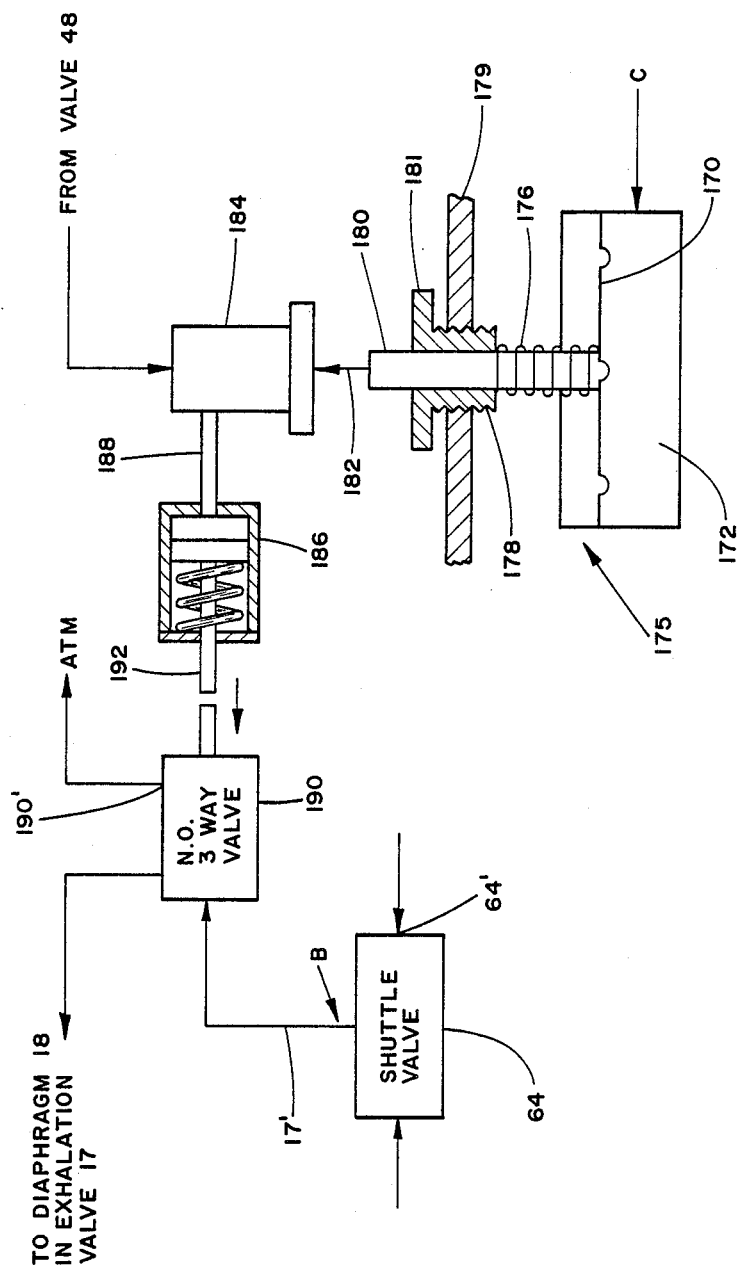
FIG. 3 is a schematic diagram similar to a portion of FIG. 1, showing on a larger scale the pressure limiting circuit of the ventilator system, employing the exhalation valve of the patient breathing circuit as an instant gas dumping means.

Referring now to the drawings wherein like reference characters designate like or corresponding parts throughout, there is illustrated in FIG. 1 a ventilator system comprising a pneumatic patient breathing circuit 100', a pneumatic PEEP-ASSIST circuit 150, and association pneumatic and electrical circuit components. By comparing FIG. 1 herein with FIGS. 1A and 1B of my prior U.S. Pat. No. 4,141,354, it will be noted that two modifications according to the invention have been made. First, the ASSIST circuit 200 and the PEEP circuit 300 of U.S. Pat. No. 4,141,354 have been modified and combined to form the PEEP-ASSIST circuit 150 of FIG. 1 herein. Second, the Patient Breathing Circuit 100 of U.S. Pat. No. 4,141,354 has been modified as shown in FIGS. 1 and 3 herein to provide a new pressure limiting arrangement in the present Patient Breathing Circuit 100', so that exhalation valve 17 of the Patient Breathing Circuit 100' serves as an instant gas dumping means.

Since the basic arrangement and functional operation of the ventilator system described in U.S. Pat. No. 4,141,354 have been maintained in the present system, reference will be made to that patent where necessary, for discussion of details explained in the patent; and this description will be largely confined to the modifications embodying the present invention.

Figure 2:
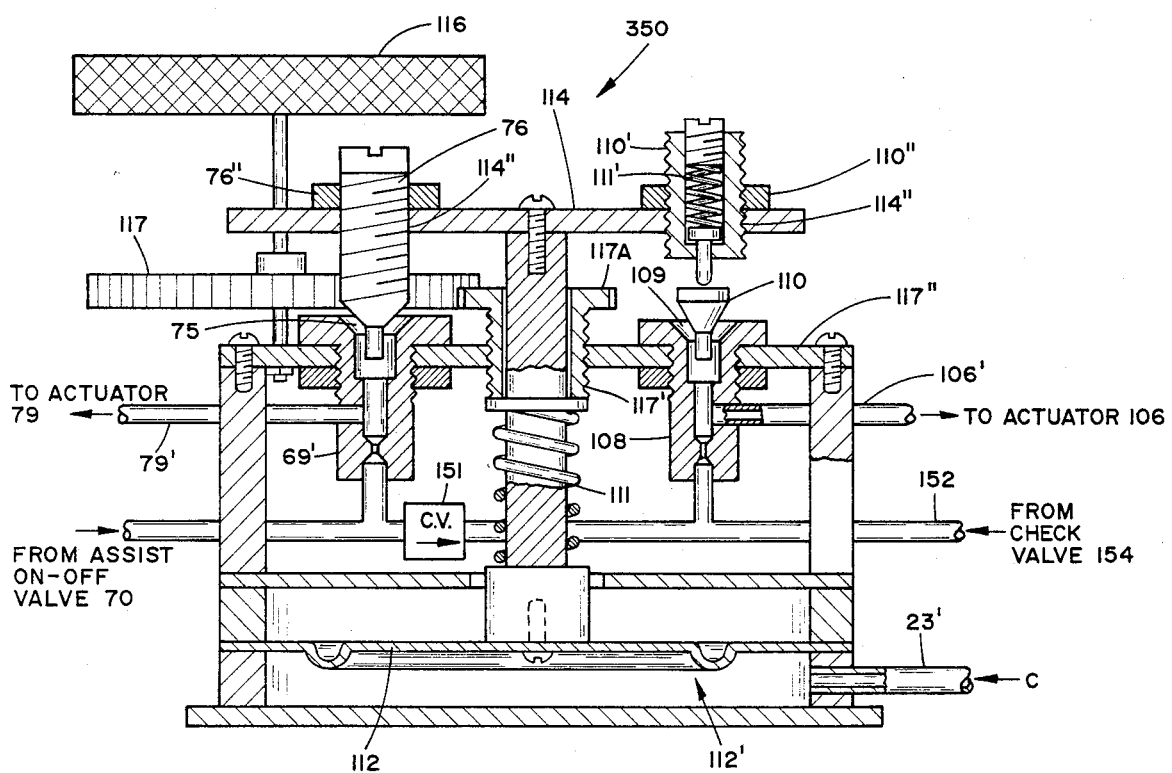
FIG. 2 is a vertical sectional view of a PEEP-ASSIST sensor module assembly according to the invention.

Referring now to FIGS. 1 and 2, a PEEP-ASSIST module 350 has a diaphragm 112 adjustably biased by a spring 111 on a shaft or rod 113'. The spring 111 is acted on by a gas pressure C existing in a patient breathing tube 1'. The pressure C is applied via a line 23' from a chamber 23a in an isolation unit 23 in a Patient Breathing Circuit 100'. Thus, the diaphragm 112 can raise and lower a support arm 114 via the rod 113' connected thereto. The support arm 114 carries an ASSIST needle 76 and a spring loaded actuator 110' loaded by the spring 111'. The actuator 110' operates PEEP needle 110. The needles 76 and 110 can respectively seal a vent 75 in an ASSIST sensor 69' (A.S.) and a vent 109 (FIG. 2) in a PEEP sensor 108 (P.S.) to cause operation of an ASSIST actuator 79 and a PEEP actuator 106. The ASSIST actuator 79 in the circuit 150 is connected to the sensor 69' via a conduit 79'. The PEEP actuator 106 in the circuit 150 is connected to the sensor 108 via a conduit 106'. Reference should be made to U.S. Pat. No. 4,141,354 for a detailed discussion of the results and effects of operating the actuators 79 and 106.

The PEEP needle 110 is set to actuate and seal the vent 109 prior to the ASSIST needle 76 sealing the vent 75. The spring loaded PEEP actuator 110' provides the needle 110 with the necessary additional mechanical movement required to permit sealing the ASSIST vent 75 after the PEEP vent 109 is sealed. The differential in sealing is factory adjusted so that the additional pressure to seal the ASSIST vent 75 after the PEEP vent 109 is sealed is 2 cmH$_2$O suction applied to the underside of the diaphragm 112 in a chamber 112'. This is accomplished by the physical locations of the needle 76 and the PEEP spring loaded actuator 110' with respect to the support arm 114. The threaded needle 76 is adjusted by turning it in a threaded hole 114' in the arm 114, and then the needle position is locked by a nut 76". Similarly the threaded actuator 110' is turned in a threaded hole 114" in the arm 114 and then is locked by a nut 110".

The absolute magnitude of the pressure in the chamber 112' under the diaphragm 112 for initial actuation and sealing of the PEEP vent 109 is determined by the bias placed on the main spring 111 bearing on the diaphragm 112. A gear 117A drives a bias adjusting screw 117'. The setting of the gear 117A is controlled by a mating gear 117 turned by an adjustment knob 116. Reference should be made to the description of FIG. 8 in U.S. Pat. No. 4,141,354 for further detailed explanation as to operation of the adjustment knob 116 and the gears 117, 117A.

Minimum bias is placed on the spring 111 when breathing ASSIST only is desired. Increased bias on spring 111 is employed to obtain PEEP, i.e. positive end expiratory pressure (with or without breathing ASSIST). In practice the adjusting knob 116 is restricted in travel by mechanical stops to one revolution of 360 degrees. The first 60 degrees of movement is used to adjust the ASSIST inspiratory effort in the −5 cmH$_2$O to 0 cmH$_2$O range. Continued rotation of the knob 116 obtains PEEP values of 0 cmH$_2$O to 25 cmH$_2$O, with breathing ASSIST available at the −2 cmH$_2$O differential.

FIG. 1 shows the pneumatic circuit 150 for PEEP-/ASSIST. Gas for powering the PEEP/ASSIST module 350 is derived from a 4-way valve 48 during exhalation, designated as flow A here as well as in U.S. Pat. No. 4,141,354. The PEEP on-off valve 104' is now a 3-way valve which permits powering gas to flow to a PEEP sensor 108 when the valve 104' is in ON position, or to flow to an ASSIST on-off switch 70 via a miniature shuttle valve 70' when the valve 104' is in OFF position. The shuttle valve 70' is similar to a shuttle valve 65 described in U.S. Pat. No. 4,141,354 and shown in FIG. 6 of the patent.

Assume now that it is desired to only have breathing ASSIST, that is, the ventilator system is to be employed as a breathing assistor or breathing assistor-controller. The PEEP on-off valve 104' is set in OFF position, while the ASSIST switch 70 is place to ON position to power the ASSIST sensor 69'. The bias of the spring 111 is adjusted by a knob 116 and gears 117, 117A for minimum magnitude, at which magnitude the spacing of the needle 76 above the vent 75 has been preset; so that a negative suction of −5 cmH$_2$O under the diaphragm 112 is required to seal off the vent 75 to obtain an assisted inspiratory breath. As the spring bias is increased, a lesser amount of suction is required to effect a seal of the vent 75; and the inspiratory effort required to initiate inspiration is reduced continually and adjustably from −5 cmH$_2$O to 0 cmH$_2$O (during the initial 60 degree rotation of the adjusting knob 116).

If the bias of the spring 111 is increased by additional movement of the adjusting knob 116, the ASSIST sensor vent 75 will seal at positive values of breathing gas pressure and the ventilator will go into self-oscillation which is a nonusable or undesirable condition of operation. If however, PEEP is ON as well, as described below, self-oscillation will not occur, since the needle 76 cannot seal the ASSIST sensor 69' until the PEEP sensor 108 is sealed, locking the patient circuit at this PEEP level. ASSIST action cannot occur until an additional suction of −2 cmH$_2$O is applied by the patient's inspiratory effort.

If the PEEP on-off valve 104' is placed ON, driving gas A can only go to the PEEP sensor 108. No driving gas A is available initially at the input of the ASSIST On-Off switch 70. Only after the PEEP sensor vent 109 is sealed and the PEEP actuator 106 operates the normally closed valve 103 to provide sealing gas B to the exhalation valve diaphragm 18, is gas also supplied to the other leg of the shuttle valve 70', thereby supplying driving gas to the inlet of the ASSIST On-Off switch 70. Thus, if both PEEP and ASSIST are ON, the ASSIST cannot be actuated until the PEEP sensor 108 has sent out a PEEP signal, thereby preventing pressure transients in the breathing gas circuit from causing premature operation of the ASSIST before PEEP is locked in, with resulting cycling instability.

The PEEP-ASSIST circuit 150 has been further improved to establish a reference level of ASSIST, whether or not PEEP is employed. It will be noted that if only ASSIST is placed ON that both the ASSIST and PEEP sensors 69', 108 are powered. The PEEP sensor is powered by means of the gas entering this sensor via a check valve 151 in a line 152 connecting the two sensors. A second check valve 154 prevents the powering gas from reaching a normally closed valve 103. Thus even though the PEEP sensor 108 is powered, its vent 109 is sealed, and its actuator 106 functions, no powering gas is available to the normally closed valve 103 to be directed to a diaphragm 18 of an exhalation valve 17, to establish a PEEP pressure level. The ASSIST sensor vent 75 is sealed after the PEEP sensor vent 109 is sealed by an inspiratory effort of the patient.

The functioning of the PEEP/ASSIST module 350 is identical whether PEEP is ON or OFF when ASSIST is employed. This arrangement guarantees that a given setting by a knob 116 of a control gear 117 which sets the position of a biasing screw 117', always relates to a given value of ASSIST inspiratory effort. If the PEEP sensor 108 were not simultaneously powered, less force would be required to seal off its vent 109, and correspondingly less suction under the diaphragm 112 would be needed to initiate an ASSIST inspiration, than when both sensors are powered. By always powering the PEEP sensor 108 when breathing ASSIST is desired, the effort to initiate an inspiration is established at the same level, whether or not PEEP is employed at a given bias setting of the spring 111.

Figure 1A:
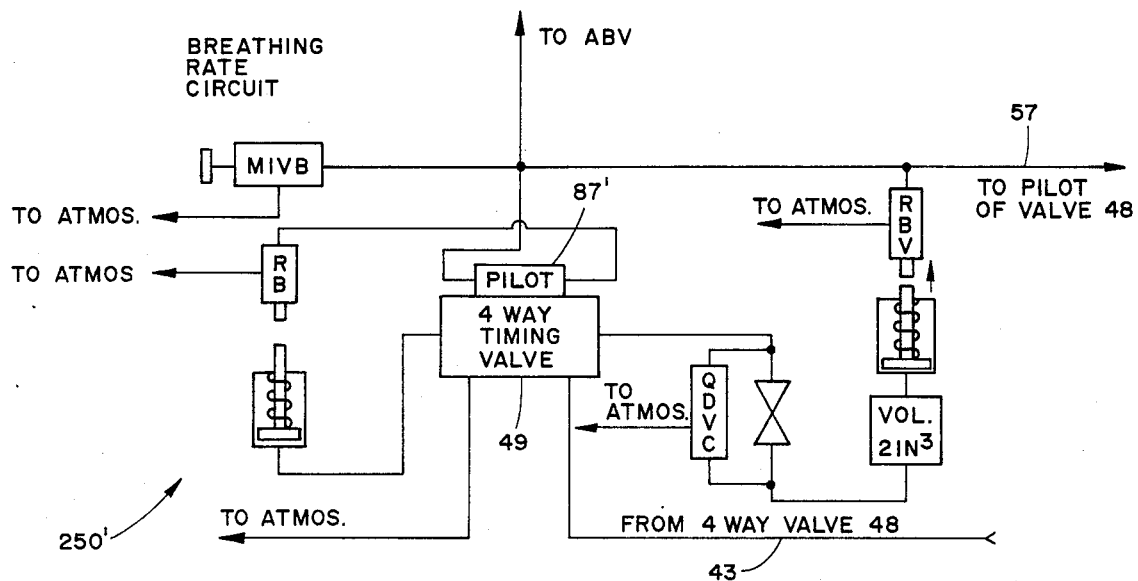
FIG. 1A is a schematic diagram of a breathing rate monitoring and control circuit used in association with the ventilator system of FIG. 1.

In FIG. 1A is shown a breathing rate circuit 250' associated with a patient breathing circuit 100' and the PEEP/ASSIST circuit 150 of FIG. 1. This circuit is constructed and operates in the same manner as described in my prior U.S. Pat. No. 4,141,354 so those details will not be repeated here. The circuit 250' includes a 4-way timing valve 49 operated by a pilot 87'. The internal construction of this valve is explained in my earlier U.S. Pat. No. 3,251,359 and its functioning in the present system is substantially the same as described in U.S. Pat. No. 4,141,354 to which reference should be made. The valve 48 is involved with the ASSIST, PEEP, and gas dumping functions as explained herein. Lines 43 and 57 are connected between a valve 48 and the valve 49.

In column 4 of U.S. Pat. No. 4,141,354 is described the operation of a pressure limiting spring loaded valve 26 in the Patient Breathing circuit 100 for dumping breathing gas when pressure rises excessively. As indicated above this type of valve has a throttling action which retards quick dumping of gas, so that it cannot be absolutely certain that the pressure limit setting will not be exceeded, particularly during operation at high inspiratory flow rates. This situation has been remedied herein by eliminating the spring loaded gas dumping valve 26 from the present Patient Breathing Circuit 100'. Instead, quick gas dumping is accomplished via the exhalation valve 17. The exhalation valve 17 offers no retard to quick dumping of gas at any excessive pressure.

If the sealing gas B to a diaphragm 18 of the exhalation valve 17 is cut off when the pressure in a patient hose 15' reaches a predetermined limiting value, then excess gas can quickly dump through the exhalation valve 17. When the pressure falls below the pressure limiting value, it is desired to again direct sealing gas B to the diaphragm 18 to close the exhalation valve 17, stopping gas dumping, and directing all breathing gas to the patient. The exhalation valve 17 can be made to open and shut rapidly to ensure that the breathing gas is limited to the preset value. Such limiting action is very obvious to the operator of the system, since it is observable on the reading of a pressure gauge 24, in instantaneous accelerations and decelerations of movement or a bellows 1 due to loading and unloading the bellows 1 when the exhalation valve 17 opens and shuts, and due to the characteristic audible noise signal made when the exhalation valve 17 opens and shuts.

The circuit which accomplishes pressure limiting in the present ventilator system is shown schematically in FIGS. 1 and 3. A spring biased diaphragm 170 closes a chamber 172 in a pressure limit module 175. The construction of this module has many features similar to the PEEP/ASSIST module 350 described above. The diaphragm 170 is biased by a spring 176 against a threaded adjustment nut 178 mounted in a stationary support plate 179 like a stationary plate 117" in the module 350. A shaft 180 of the module 175 extends through a nut 178 and is axially movable. The shaft 180 engages and moves a needle 182 to open and close a vent port of a pressure limit sensor 184 constructed like the ASSIST and PEEP sensors 69', 108 respectively, as shown in FIG. 2. When the vent port of the sensor 184 is closed, a pressure limit actuator 186 is operated via a conduit 188 to operate and close a normally open 3-way value 190. The actuator 186 is similar in construction and function to those of the ASSIST and PEEP actuators 79 and 106. When a pressure limit actuator rod 192 is not extended up to the valve 190, gas pressure in the patient breathing circuit 100' has not exceeded the preset value. Then the valve 190 is open permitting sealing gas B for the exhalation valve 17 to be derived from a shuttle valve 64 via a line 17'. The shuttle valve 64 is powered at the port 64' by the inspiratory gas developed at the 4-way timing valve 48 shown in FIG. 1.

The sealed exhalation valve 17 causes all gas being delivered by the bellows 1 to be forced to the patient via a hose 14. Reference should be made to my prior U.S. Pat. No. 4,141,354 for a detailed description of construction and operation of the bellows 1. If the patient breathing gas pressure C exceeds the preset value or magnitude of the Pressure Limiting module 175 as determined by the bias of the spring 176 on the diaphragm 170, the higher pressure cause the diaphragm 170 to rise, thereby causing a needle 182 to seal the vent port of the Pressure Limit sensor 184. This causes the Pressure Limit actuator 186 to close the normally open valve 190. In this valve position, sealing gas B cannot enter via line 17' to the diaphragm 18 in the exhalation valve 17, while gas in the exhalation valve 17 is vented to atmosphere through the ATM port 190' of the valve 190. This causes the exhalation valve 17 to open and permit a rapid dumping of breathing gas via the ventilation meter to atmosphere until the gas pressure falls below the preset limiting value. At this time, the spring loaded diaphragm 170 in the module 175 drops; the needle 182 opens the vent port of the sensor 184; the acuator rod 192 retracts and the valve 190 assumes normally open position. Sealing gas B again enters the exhalation valve 17 causing it to close and stop the gas dumping action.

From the foregoing it can be seen that if the pressure of gas in the patient hose 15' exceeds the desired preset limit, the fluctuating of the gas pressure C causes a chain action which effectively opens and shuts the exhalation valve 17 to limit the maximum pressure that can be built up in the patient breathing circuit 100'. The bias of the spring 176 is normally adjusted by rotating an adjusting knob 181 of the nut 178 to permit a selected value of pressure limiting in the range of 25 to 100 cmH₂O to be chosen by the operator of the ventilator system.

It should be understood that the foregoing relates to only a limited number of preferred embodiments of the invention, which have been by way of example only and that it is intended to cover all changes and modifications of the example of the invention herein chosen for the purpose of the disclosure, which do not constitute departures from the spirit and scope of the invention.

What is claimed is:

1. A ventilator system for controlling and assisting a patient in breathing, comprising:
   a pneumatic first circuit having an exhalation means for receiving and conducting an exhaled gas from a patient and and inhalation means for providing and conducting an inhalation gas to said patient; and
   a pneumatic positive end expiratory pressure and breathing assist second circuit connected to said inhalation means of said first circuit, said second circuit comprising:
   a chamber connected to said inhalation means for receiving the inhalation gas pressure therefrom;
   a diaphragm in said chamber;
   an axially movable rod having one end coupled to said diaphragm;
   a spring having one end supported on said diaphragm and surrounding said one end of said rod;
   a support arm connected to the other end of said rod;
   first and second spaced needles extending from said arm;
   a stationary support, said other end of said spring bearing against said stationary support;
   a breathing assist pressure sensor and a positive end expiratory pressure sensor, both of said pressure sensors connected to said support and having individual vents variably closable by said first and second needles respectively, whereby the bias in said spring is translated to said needles by said rod and said support arm to keep said vents of said sensors closed until said inhalation pressure is greater then the spring bias on said diaphragm whereby said vents of said sensor are opened; and
   means for adjusting the bias of said spring, so that operating points of both of said sensors are coordinated and track at a fixed pressure differential.

2. A ventilator system as defined in claim 1, further comprising:
   a threaded nut rotatably mounted in said stationary support and surrounding said rod, the other end of said spring bearing against said nut; and wherein said means for adjusting the bias in said spring comprises an adjustable rotatable control knob and means operatively coupled to said control knob and engaging said nit for turning the same and thereby change the tension in said spring, whereby said operating points of both of said sensors are set in coordination by selectively adjusting sad control knob.

3. A ventilator system as defined in claim 2, further comprising adjustment means mounted on said support arm and arranged for adjusting and locking said first needle in position in said vent in said breathing assist pressure sensor.

4. A ventilator system as defined in claim 3, further comprising a needle actuator mounted on said support arm and engaging said second needle, said needle actuator having a spring and a means for adjusting the bias thereof thereby to set the minimum operating point of said positive end expiratory pressure sensor.

5. A ventilator system as defined in claim 1, wherein said exhalation means includes a valve and a hose, one end of said hose being connected to said valve and to said inhalation means, and the other end thereof operatively connected to said patient, and wherein said pneumatic first circuit further comprises another pneumatic circuit connected to said inhalation means for sensing the inhalation gas pressure and having means connected to said exhalation valve for instantly dumping breathing gas at predetermined maximum pressure without retard and without throttling.

6. A ventilator system as defined in claim 1, wherein said exhalation means in said pneumatic first circuit further includes means for instantly dumping exhaled gas at predetermined maximum pressure, comprising
   an exhalation valve;
   another module assembly, having another chamber said other chamber connect to said first circuit for receiving the inhalation gas pressure therefrom;
   another diaphragm in said other chamber;
   another axially movable rod having one end connected to said other diaphragm;
   a rod spring having one end supported on said other diaphragm and surrounding said one end and a portion of said other rod;
   another stationary support, the other end of said rod spring bearing against said other stationary support;
   an adjustment member connected to said support and surrounding a part of said other rod, with the other end of said rod spring bearing against said adjustment member;
   a pressure limit sensor disposed for actuation by movement of said rod in response to movement of said other diaphragm;
   a pressure limit actuator connected to and operated by said pressure limit sensor; and
   another valve connected to said pressure limit actuator and arranged to coact with said exhalation valve for instantly dumping breathing gas to atmosphere via said exhalation valve when said breathing gas pressure rises to said predetermined maximum pressure.

7. A breathing assistor and positive end expiratory pressure module assembly for a ventilator system comprising:
   a chamber for receiving the inhalation gas pressure of said patient;
   a diaphragm for closing said chamber;
   an axially movable rod coupled at one end to said diaphragm;
   a spring having one end supported by said diaphragm and surrounding said one end of said rod;
   a support arm connected to the other end of said rod;
   first and second needles extending from said arm;
   a stationary support, the other end of said rod spring bearing against said stationary support;
   a breathing assist pressure sensor and a positive end expiratory pressure sensor, both of said pressure sensors connected to said support and having individual vents variably closable by said first and second needles respectively, depending on the magnitude of pressure of said breathing gas applied to said diaphragm via said chamber; and
   means for adjusting the bias in said spring, so that operating points of both of said sensors are coordinated and track at a fixed pressure differential, whereby a predetermined inspiratory effort by the patient will initiate an inspiration, and whereby a predetermined reduction in breathing gas pressure received from the patient will also initiate an inspiration.

8. A breathing assistor and positive end expired pressure module assembly as defined in claim 7, further comprising:
a threaded nut rotatably mounted on said stationary support, the other end of said spring bearing against said nut; and wherein said means for adjusting bias in said spring comprises an adjustable control knob operatively coupled to said nut for turing the same against tension in said spring, whereby said operating points of both of said sensors are set in coordination by selectively setting control knob.

9. A breathing assistor and positive end expiratory pressure module assembly as defined in claim 8, further comprising adjustment means mounted on said support arm and arranged for adjusting and locking said first needle in position in said vent in said breathing assist pressure sensor.

10. A breathing assistor and positive end expiratory pressure module assembly as defined in claim 9, further comprising a needle actuator mounted on said support arm and engaging said second needle, said needle actuator having a spring means and an adjusting means for changing the bias thereof to set the minimum operating point of said positive end expiratory pressure sensor.

11. A breathing assistor and positive end expiratory pressure module assembly as defined in claim 8, further comprising gear means operatively coupling said control knob and said nut for turning said nut against tension in said spring.

* * * * *